US009156067B2

United States Patent
Talarico

(10) Patent No.: US 9,156,067 B2
(45) Date of Patent: Oct. 13, 2015

(54) TOOTHBRUSH STEAM CLEANING CONTAINER

(76) Inventor: Margaret Talarico, Lewiston, NY (US)

(*) Notice: Subject to any disclaimer, the term of this patent is extended or adjusted under 35 U.S.C. 154(b) by 666 days.

(21) Appl. No.: 13/525,430

(22) Filed: Jun. 18, 2012

(65) Prior Publication Data

US 2012/0318307 A1    Dec. 20, 2012

Related U.S. Application Data

(60) Provisional application No. 61/497,574, filed on Jun. 16, 2011.

(51) Int. Cl.
- A46B 17/06 (2006.01)
- A47K 1/09 (2006.01)
- A61L 2/07 (2006.01)
- B08B 3/10 (2006.01)

(52) U.S. Cl.
CPC . B08B 3/10 (2013.01); A46B 17/06 (2013.01); A46B 17/065 (2013.01); A47K 1/09 (2013.01); A61L 2/07 (2013.01)

(58) Field of Classification Search
CPC ........ A46B 17/06; A46B 17/065; A47K 1/09; A61L 2/07; B08B 3/10
USPC ............................................. 134/105; 422/26
See application file for complete search history.

(56) References Cited

U.S. PATENT DOCUMENTS

| | | |
|---|---|---|
| 3,734,106 A | 5/1973 | Zimmerman |
| 4,214,657 A | 7/1980 | Winston |
| 4,473,152 A | 9/1984 | Jump, Jr. |
| 4,585,119 A | 4/1986 | Boyington |
| 4,759,383 A | 7/1988 | Phillips |
| D301,099 S | 5/1989 | Morris |
| 4,845,859 A | 7/1989 | Evans |
| 4,915,219 A | 4/1990 | Ottimo |
| 5,107,987 A | 4/1992 | Palazzolo |
| 5,852,879 A | 12/1998 | Schumaier |
| 6,119,854 A * | 9/2000 | Prentice et al. ............ 206/209.1 |
| 6,565,819 B1 | 5/2003 | Herrera |
| 6,702,113 B2 | 3/2004 | Marino |
| 6,874,247 B1 | 4/2005 | Hsu |
| 6,994,212 B2 | 2/2006 | Bar Noy |
| 7,225,559 B1 | 6/2007 | Padilla |
| 2003/0034459 A1 | 2/2003 | Bonin |
| 2004/0126274 A1* | 7/2004 | Song et al. ...................... 422/26 |
| 2004/0258559 A1* | 12/2004 | Paskal et al. .................... 422/26 |
| 2007/0140896 A1 | 6/2007 | Baggett |

* cited by examiner

*Primary Examiner* — Joseph L Perrin
*Assistant Examiner* — Levon J Shahinian
(74) *Attorney, Agent, or Firm* — Daniel Boudwin; Global Intellectual Property Agency LLC

(57) ABSTRACT

Disclosed is a toothbrush storage and sanitizing container, comprising a housing having a lower portion and an upper portion. The lower portion comprises an interior fluid reservoir and an open interior between the reservoir and the walls of the housing for retaining the handles of at least one toothbrush. The upper portion is a removable enclosure that supports the toothbrush heads in an upstanding configuration. A nozzle device connects the reservoir to the upper portion of the housing, while a heating element within the reservoir rapidly heats and vaporizes the water therein. High pressure and high temperature steam is communicated through the nozzle ports in the upper portion of the housing to subject the toothbrush heads to a burst or continuous spray of steam for cleaning and sanitation purposes.

8 Claims, 2 Drawing Sheets

TOOTHBRUSH STEAM CLEANING CONTAINER

CROSS REFERENCE TO RELATED APPLICATION

This application claims the benefit of U.S. Provisional Application No. 61/497,574 filed on Jun. 16, 2011, entitled "Sparkling Bristles." The patent application identified above is incorporated here by reference in its entirety to provide continuity of disclosure.

BACKGROUND OF THE INVENTION

1. Field of the Invention

The present invention relates to toothbrush containers and sanitizers. More specifically, the present invention pertains to a toothbrush sanitizing container having a heating means for vaporizing a quantity of water and utilizing the steam to clean at least one toothbrush within the interior of the assembly.

Toothbrush containers and storage devices are a well described device in the prior art. These devices provide an enclosed or semi-enclosed structure that shrouds the head of several toothbrushes to prevent contamination and contact with substances that may be harmful for human consumption. Generally toothbrushes are stored in a bathroom setting and in close proximity to a toilet or sink, wherein water splatter and contaminates are readily dispersed through the air. Protecting the bristle portion of a toothbrush is of key importance with respect to preventing contamination in these environments; however simple enclosures do no prevent contaminates such as bacteria and fungi from spreading along the bristles after an initial exposure. This exposure may occur when the toothbrush is in use, after which the brush is placed into the enclosed housing of a holder and left untreated.

More advanced brush holders have been developed to combat this known problem, and generally relate to devices that incorporate a disinfectant solution and further to a means of drying the brushes after use to prevent mold development. Those that utilize disinfectant solution include a reservoir of solution to immerse the bristles of a toothbrush, loosening debris and eliminating germs from the bristles between uses. Drying containers provide a heating source and generally and exhausting means rapidly dry moistened bristles and to evacuate the heated air from the container, which prevents festering of the bristles and fungi from forming thereon, which is a common occurrence in dimly lit, moistened environments.

The present invention pertains to a toothbrush container that provides a sanitizing feature for the same effect, however using a heating element and reservoir of water to vaporize the water and create a high pressure, high temperature steam environment that kills germs and disinfects a plurality of support toothbrush bristles within an enclosure. A heating element on a timer switch rapidly heats a small quantity of water, which transforms into steam that is conveyed to the bristle upper portion of the enclosure to heat and kill germs and fungi from the brush heads. The enclosure itself is adapted to support a plurality of toothbrush devices in an upright and covered configuration, wherein the steam cleaning means is stored in a lower portion and activated as necessary by the user prior to or just after use of a toothbrush.

2. Description of the Prior Art

Devices have been disclosed in the prior art that relate to toothbrush disinfecting and storing containers. These include devices that have been patented and published in patent application publications. These devices generally relate to containers that utilize a cleaning solution, dryer or heater. The devices deemed most relevant to the present disclosure are herein described for the purposes of highlighting and differentiating the unique aspects of the present invention, and further highlighting the drawbacks existing in the prior art.

Specifically, U.S. Pat. No. 4,845,859 to Evans discloses a toothbrush storage and dryer device having an upright cylindrical housing sized to receive at least one toothbrush axially therein. The housing is separated into an upper chamber and lower chamber, wherein a light bulb heating source is placed within the lower chamber. The light bulb heats the lower chamber, whereafter the heated air flows across the chamber boundary to dry a toothbrush positioned within the upper chamber. The head of the toothbrush is adapted to be placed within the upper chamber to allow the heated air to dry and sterilize the brush. While providing a novel means to dry a toothbrush using a heated chamber, the Evans device fails to contemplate the use of superheated steam as a means to sterilize the toothbrush head. The present invention provides a structure that quickly heats a body of water to create steam, whereafter the high pressure steam is sent through nozzles and into a chamber housing at least one toothbrush head for cleaning.

Similar to the Evans device, U.S. Pat. No. 7,225,559 to Padilla discloses a toothbrush dyer device comprising a substantially hollow housing having an interior chamber adapted to accept a plurality of toothbrushes via retaining clips, along with a blower/heater mechanism that circulates warm air through the interior chamber. The interior chamber provides a means to retain the toothbrushes, while the heater/blower mechanism dries the items. A thermostat is further incorporated into the housing to control the operation of the blower/heater mechanism to prevent overheating, while a magnetically latching door provides a means of access and closure for the interior chamber. The Padilla device includes similar failings as the Evans device, wherein no steam means of sterilizing the toothbrush heads is provided.

U.S. Pat. No. 6,874,247 to Hsu discloses another toothbrush dryer device comprising a housing having a cover that defines an interior of the housing, along with a heating device for heating a drying pan formed along the bottom portion of the housing that transfers heating to a plurality of suspended toothbrushes connected to the pan. Air is further heated within the housing interior, while a thermosiphon discharges moisture outwardly from the housing to prevent bacteria or fungi contamination. The structure of the housing is one that encloses the head of several toothbrushes, while each brush is suspended from a plurality of recesses along the bottom portion of the housing. The Hsu device discloses a drying device that includes a heating pan, but lacks the ability to superheat a container of water for creating steam, which is then utilized as a cleaning agent.

Further, U.S. Pat. No. 5,107,987 to Palazzolo describes a toothbrush holder and disinfectant device, wherein a main container is disclosed having an internal chamber filled with a disinfectant solution for immersing a toothbrush head therein of loosening material and debris therefrom. The base of the container chamber comprises a plurality of upstanding protrusion support elements, which are spaced apart to support a toothbrush from the base of the chamber. Spaces between the protrusions allow sediment and debris to settle, while the toothbrush head is suspended thereabove by the protrusions and away from the settled debris that is trapped within the protrusions. The Palazzolo device describes a novel means of immersing and separating foreign material from a toothbrush head, which improves sanitation and contamination of the toothbrush head while in storage. This device, however, while providing a toothbrush container, diverges in spirit and structure from the present invention, which pertains to a steam cleaning toothbrush container device.

Finally, U.S. Pat. No. 6,565,819 to Herrera discloses a toothbrush sanitizer that rapidly sanitizes a toothbrush using a housing containing a reservoir of water, a tube connected for carrying the water to a pan mounted along the lower portion of the housing. The pan is heated by a heater device, which rapidly vaporizes a small amount of water delivered from the tube. A motor rotates an armature that allows a small quantity of water to be delivered onto the pan, while a timer controls the heating element and thus the vaporizing operation. The steam is utilized to sanitize the bristles of a toothbrush that is downwardly supported above the pan. The Herrera device, while utilizing steam as a means to sanitize, utilizes a structure that is adapted to function using droplets of water dispensed from a tube, as opposed to a heated reservoir of water that is carried through a series of nozzles for sanitizing a plurality of toothbrush assemblies in the upper portion of the present invention.

The present invention comprises an internal chamber of water that is adapted to be rapidly heated and vaporized into steam, whereby the steam is forced through aperture nozzles to an upper enclosed portion wherein at least one toothbrush head is positioned. The high temperature steam cleans the bristles of the brush head by removing debris and killing bacteria and fungus. The enclosure over the upper portion of the container is removably securable during operation, while the heating means is maintained by a timer switch to prevent overheating and fire risk. In light of the aforementioned prior art, it is submitted that the present invention substantially diverges in design elements from the prior art, and consequently it is clear that there is a need in the art for an improvement to existing toothbrush cleaning and container devices. In this regard the instant invention substantially fulfills these needs.

SUMMARY OF THE INVENTION

In view of the foregoing disadvantages inherent in the known types of toothbrush containers and cleaners now present in the prior art, the present invention provides a new toothbrush cleaner wherein the same can be utilized for providing convenience for the user when steam cleaning the bristles of a toothbrush within an enclosed housing.

It is therefore an object of the present invention to provide a new and improved toothbrush steam cleaner device that has all of the advantages of the prior art and none of the disadvantages.

It is another object of the present invention to provide a toothbrush steam cleaner device that stores a plurality of toothbrushes in an enclosed environment, wherein the environment is a controlled area that is sanitized using a high temperature injection of steam.

Another object of the present invention is to provide a toothbrush steam cleaner device that rapidly heats and vaporizes a small quantity of water within a reservoir, creating a stream or bust of steam into an upper portion for cleaning and sterilization purposes.

Yet another object of the present invention is to provide a toothbrush steam cleaner that incorporates a heating element having a timer switch and means of deactivating after a given interval to prevent risk of overheating or fire.

A final object of the present invention is to provide a toothbrush steam cleaner that is of simple construction for ease of manufacturing and reduced cost to the consumer.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
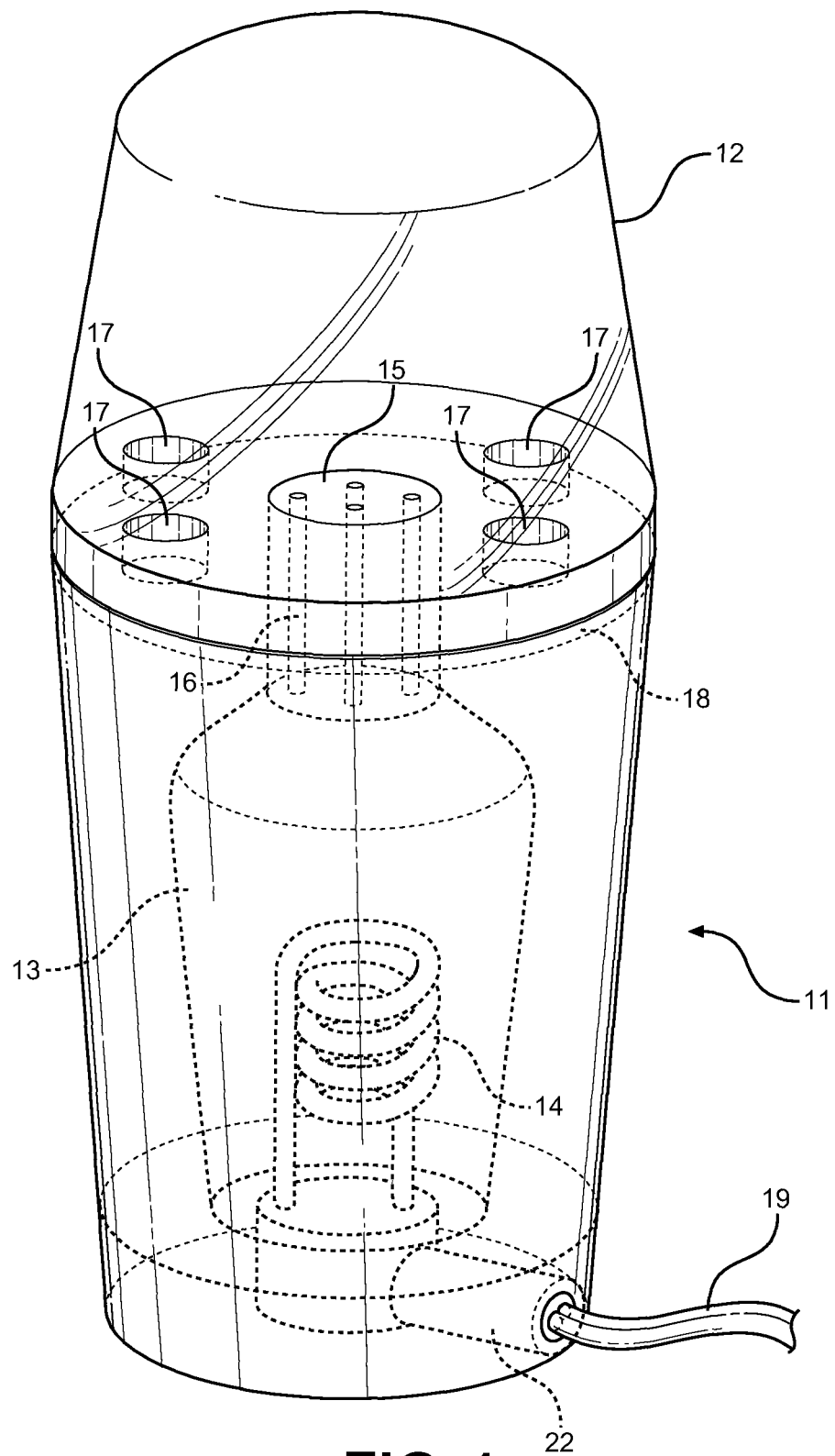
FIG. 1 shows a perspective view of the present invention, including its internal structure and means of delivering high temperature steam to its upper enclosure portion.

Reference is made herein to the attached drawings. Like reference numerals are used throughout the drawings to depict like or similar elements of the toothbrush steam cleaner. For the purposes of presenting a brief and clear description of the present invention, the preferred embodiment will be discussed as used for storing and sanitizing a plurality of toothbrushes using an enclosure and steam generating means. The figures are intended for representative purposes only and should not be considered to be limiting in any respect.

Referring now to FIG. 1, there is shown a perspective view of the toothbrush steam cleaner of the present invention. The device comprises an upstanding enclosure having an interior volume separated into an upper portion 12 and a lower portion 11. The upper portion 12 comprises a removably sheltered area for which to position the brush heads of a plurality of toothbrushes, wherein the brush handle portions are supported by a shelve having a plurality of apertures 17 adapted to accept the handle portion each toothbrush. The upper portion includes a removably connected lid that is preferably hingedly attached, allowing access to the shelf for placement and withdrawal of brushes into the support apertures 17. The lower portion 11 of the enclosure comprises an open interior section adapted to accept that handles of each toothbrush, along with a central reservoir 13 of water. The reservoir 13 is centrally mounted within the lower portion and includes a heating element 14 therein, a timer switch 22 and electrical connectivity 19 for powering the heating element. Connecting the upper and lower portions of the enclosure is a central conduit 15 that includes a plurality of apertures 16 or nozzles that are of reduced cross sectional area with respect to the conduit 15 diameter. The reservoir 13 is adapted to accept a small quantity of water, while the heating element 14 rapidly heats and vaporizes the water into high temperature steam. The steam fills the reservoir volume and is forced through the apertures of the conduit 15 and into the upper enclosed portion 12. The high temperature burst or stream of steam cleans and disinfects the brush heads of any toothbrush positioned within the upper enclosure.

The heating element 14 is an electrical resistance element that rapidly heats and vaporizes the small quantity of water into steam. The narrow diameter nozzles 16 in the central conduit ensure the heated steam is accelerated and forced into the upper enclosure 12 for sterilization purposes. A timer switch 22 attached to the heating element 14 opens the electrical connection and ceases the flow of current through the element, and thus deactivates the heating means of the device after a given time interval. This safety feature prevents the device from running continuously or overheating, which would otherwise create a fire risk or consume unwanted amounts of energy. An alternative to the a timer switch is a feedback switch, wherein the temperature of the reservoir is monitored and sends a shutoff signal to the switch 22 upon reaching a threshold operating temperature. It is desired to disclose a means of regulating the time interval or operating temperature of the heating element without limiting this means to a specific set of electronic elements or placement thereof along the enclosure housing. One skilled in the art of electronic switches and appliances utilizing heating elements would readily recognize a heating element timer and temperature feedback circuit appropriate for the given device.

In an embodiment of the present enclosure, the reservoir 13 is refillable via an access panel along one side of the enclosure lower portion 11. In another embodiment, the upper portion 12 and shelf portion are threadably connected 18 to the lower portion and removable therefrom to reveal the reservoir 13, conduit 15 and interior portion of the enclosure lower portion 11 adapted to house the handle of each toothbrush placed therein. The conduit 15 may further be threadably connected to the upper portion of the reservoir 13, allowing the conduit to be removed and the user to access the upper portion of the reservoir for refilling with a quantity of water. Either embodiment includes access to the lower portion opening interior area to allow cleaning of this area, wherein toothpaste and grime may develop in this area from the handle portions of the brushes are placed therein.

Figure 2:
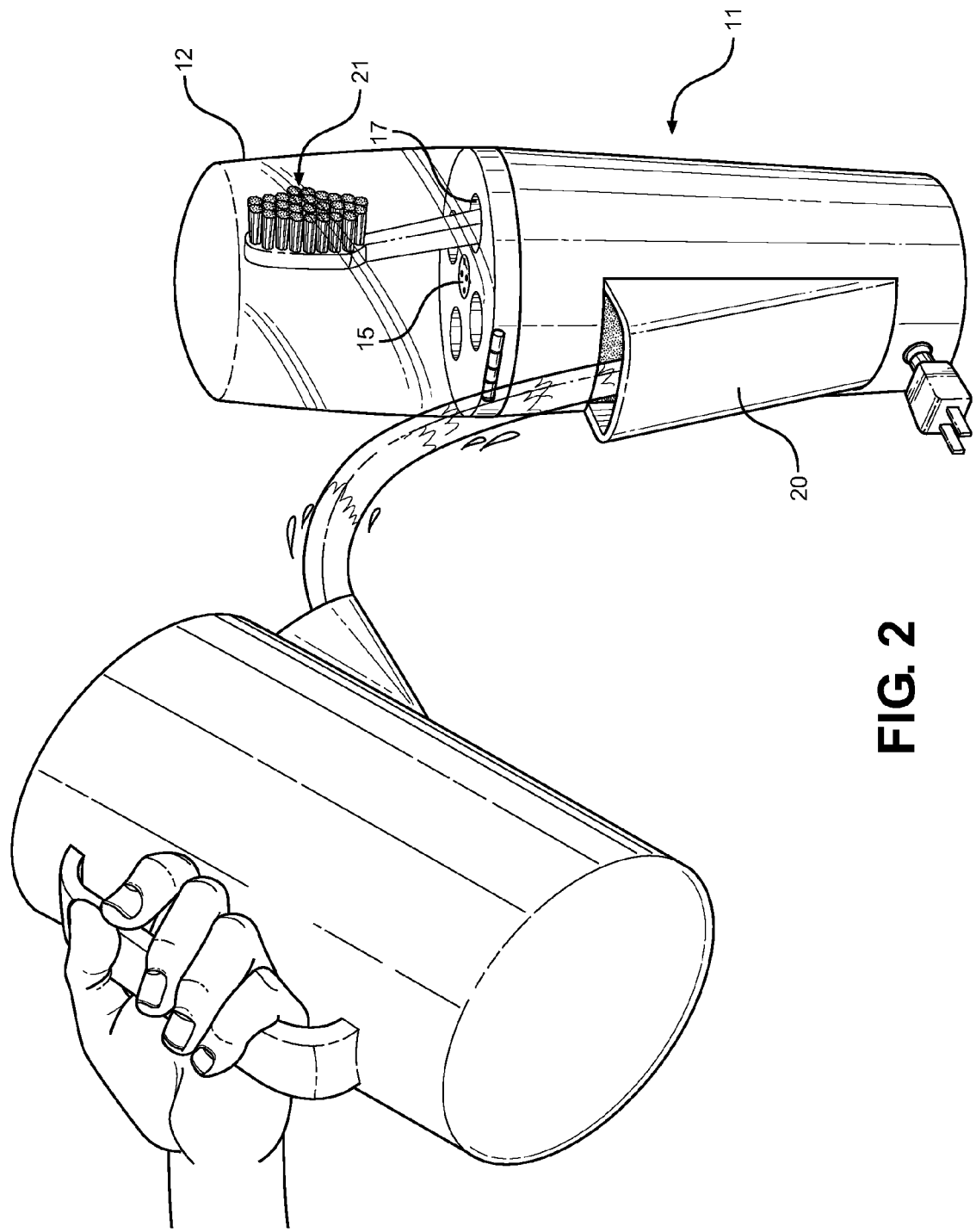
FIG. 2 shows a view of the present invention being refilled with water between uses.

Referring now to FIG. 2, there is shown a perspective view of the present invention being refilled using an embodiment of the enclosure wherein a side-entry access door 20 is provided for refilling the reservoir within the lower portion 11. In this embodiment, the reservoir is accessible from the side of the lower portion 11, wherein the access door 20 is hinged therefrom and water may be poured thereinto and closed prior to use. After the access door is closed, the heating element may be activated to rapidly heat and vaporize the water, sending bursts of steam through conduit 15 and into the upper portion 12 of the enclosure, wherein the head of a brush 21 is positioned and supported by the apertures 17 in the support shelf separating the two enclosure portions.

The internal heating element is one that rapidly heats the small quantity of water within the reservoir to a rapid boil or directly vaporizes the water into a steam, wherein the steam if builds pressure in the reservoir and forces heated and pressurized steam through the conduit nozzles and into the upper portion of the enclosure. The walls of the enclosure are preferably an insulated material such that the inner portions of the enclosure lower portion 11 are not heated, thus preventing damage to the handles of the brushes stored therein. Further, the quantity of water is minimized such that vaporization and boiling is rapid. The heating element is one that rapidly reaches operating temperature and quickly turns the small quantity of liquid into heated steam. This allows the device to quickly reach operating levels, transmit the steam into the upper portion of the enclosure and shut off after vaporizing all of the water contents for the purpose of sanitizing the brush heads.

It is understood that toothbrushes are generally left exposed in a bathroom, either placed on the sink or stored in a toothbrush holder. *E. coli* and other diseases are often spread through the air, especially in a closed environment and in such proximity to toilets in a bathroom. Using the same toothbrush continuously and without replacement or sanitization can lead to contamination or transference of diseases. Common means of cleaning such brushes include the use of chemical disinfectants, which may involve chemicals not appropriate for consumption. The present invention provides a natural sanitation and sterilization means that utilizes steam treatment to clean and reduce contaminates on toothbrush heads. The upper portion enclosure is one that incorporates a screw-on or flip-top structure, while power is transmitted to the heating element via an electrical cord connection. To reduce clutter, the electrical cord may further be retractable within the base of the enclosure lower portion.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A toothbrush steam cleaner device, comprising:
   an enclosure having an upper portion and lower portion separated by a shelf;
   said lower portion having a reservoir for storing a quantity of liquid surrounded by an open interior volume;
   said shelf having at least one aperture adapted for accepting a toothbrush handle therethrough, along with a central conduit having at least one aperture, said conduit creating a path between said reservoir and said upper portion;
   the lower portion of the enclosure having a height configured to receive a majority of one or more toothbrush handles when positioned upright through the shelf, whereby one or more toothbrush heads are separated from the lower portion by the shelf and the toothbrush heads are disposed within the upper portion of the enclosure;
   said upper portion comprising a removable lid that is adapted to removably enclose the toothbrush heads positioned through the shelf;
   said lower portion further comprising an electrical resistance heating element within said reservoir that is adapted for rapidly heating said quantity of liquid and creating steam;
   said steam adapted to travel from said reservoir, through said conduit and into said upper portion;
   said heating element adapted to receive current from an electrical cord extending from said lower portion.

2. The device of claim 1, further comprising a timer switch between said electrical cord and said heating element for turning off and on said heating element.

3. The device of claim 1, further comprising a switch between said electrical cord and said heating element for turning off and on said heating element based on an internal temperature of said reservoir.

4. The device of claim 1, wherein said upper portion enclosed volume further comprises a hinged dome structure.

5. The device of claim 1, wherein said upper portion enclosed volume further comprises a threadably attached dome structure.

6. The device of claim 1, wherein said reservoir is refillable with said quantity of liquid via a hingeable side panel that provides access to said reservoir interior through said lower portion.

7. The device of claim 1, wherein said shelf is threadably removable from said lower portion and said conduit is threadably removable from said reservoir, allowing said reservoir to be refillable through its upper region.

8. The device of claim 1, wherein said at least one conduit aperture further comprising one or more nozzles that accelerate said steam from said lower portion to said upper portion.

* * * * *